(12) United States Patent
Snowball (10) Patent No.: US 8,742,366 B2
(45) Date of Patent: Jun. 3, 2014

(54) UV LIQUID STERILISER

(75) Inventor: Malcolm Robert Snowball, Essex (GB)

(73) Assignee: Steriflow Limited, Northampton (GB)

( * ) Notice: Subject to any disclaimer, the term of this patent is extended or adjusted under 35 U.S.C. 154(b) by 190 days.

(21) Appl. No.: 13/266,444

(22) PCT Filed: Apr. 28, 2010

(86) PCT No.: PCT/GB2010/050697
§ 371 (c)(1),
(2), (4) Date: Jan. 10, 2012

(87) PCT Pub. No.: WO2010/125389
PCT Pub. Date: Nov. 4, 2010

(65) Prior Publication Data
US 2012/0097862 A1    Apr. 26, 2012

(30) Foreign Application Priority Data

Apr. 28, 2009  (GB) .................................. 0907338.8

(51) Int. Cl.
*C02F 1/32* (2006.01)
(52) U.S. Cl.
CPC ........................................ *C02F 1/32* (2013.01)
USPC .................... 250/455.11; 250/436; 422/186.3
(58) Field of Classification Search
USPC .......... 250/455.11, 436, 437, 438; 422/186.3, 422/21, 22; 210/748.11
See application file for complete search history.

(56) References Cited

U.S. PATENT DOCUMENTS

| 5,004,541 A | 4/1991 | Noll et al. |
| 5,372,781 A | 12/1994 | Hallett et al. |
| 5,675,153 A | 10/1997 | Snowball |

(Continued)

FOREIGN PATENT DOCUMENTS

| EP | 0202820 A2 | 11/1986 |
| FR | 1126278 A | 11/1956 |

(Continued)

OTHER PUBLICATIONS

Patent Corrperation Treaty, "International Search Report", Application No. PCT/GB2010/050697, dated Jul. 23, 2010, 4 pages.

(Continued)

*Primary Examiner* — Kiet T Nguyen
(74) *Attorney, Agent, or Firm* — Hickman Palermo Truong Becker Bingham Wong LLP (57) ABSTRACT

A fluid treatment apparatus particularly for sterilizing drinks comprises an elongate tubular duct (110) and an elongate UV light source (111) extending longitudinally of the duct (110). The fluid flows longitudinally of the duct (110) in a thin annular low passage (114) which extends around the UV light source (111). A mixing device (112) disposed between adjacent longitudinal portions of the duct (110) for diverts all of the fluid flowing along a first portion of the passage (114) through fluid mixing means (113,116) in the device (112) and returns the mixed fluid to a second portion of the passage (114). Micro-organisms in the thin flow of fluid are killed as they come within close proximity of the light source (111). The mixing device (112) causes all of the flow to be thoroughly mixed and returned to the flow passage (114). The provision of a plurality of mixing devices along the length of the duct (110) increases the likelihood that all microorganisms receive a sufficient lethal dose of UV radiation.

21 Claims, 8 Drawing Sheets

(56) References Cited

U.S. PATENT DOCUMENTS

| | | | |
|---|---|---|---|
| 5,725,757 A | | 3/1998 | Binot |
| 5,785,845 A | * | 7/1998 | Colaiano .................... 210/167.3 |
| 7,018,544 B2 | * | 3/2006 | Veenstra et al. ......... 210/748.11 |
| 8,080,165 B2 | * | 12/2011 | Forney .................... 210/748.11 |
| 2002/0172627 A1 | | 11/2002 | Aoyagi |
| 2003/0205454 A1 | | 11/2003 | Hlavinka et al. |
| 2008/0206095 A1 | | 8/2008 | Duthie |
| 2009/0081340 A1 | | 3/2009 | Forney |
| 2009/0084734 A1 | | 4/2009 | Yencho |
| 2011/0024365 A1 | | 2/2011 | Young et al. |

FOREIGN PATENT DOCUMENTS

| | | |
|---|---|---|
| GB | 1212633 A | 11/1970 |
| WO | WO 98/05367 | 2/1998 |
| WO | WO9913975 A1 | 3/1999 |
| WO | WO01/37675 A | 5/2001 |
| WO | WO 03/072508 A2 | 9/2003 |
| WO | WO2010125389 A | 11/2010 |

OTHER PUBLICATIONS

International Search Report in application No. PCT/Gb2012/052123 dated Mar. 6, 2013, 5 pages.

Search Report in application No. GB1115616.3 dated Dec. 17, 2012, 2 pages.

State Intellectual Property of People's Republic of China, "First Office Action" in application No. 201080018759.2, dated May 30, 2013, 2 pages.

Details of the first Office Action in application No. 2010800187592, dated May 30, 2013, 3 pages.

* cited by examiner

UV LIQUID STERILISER

This invention relates generally to the disinfection of fluids, and more particularly, but not solely to the disinfection of drinks and liquidous comestible.

At present the pasteurization technology for the drinks industry utilises thermal pasteurization, whereby a drink is elevated to a temperature which kills the micro-biological contamination in the drink and renders it fit for human consumption.

The following problems exist with thermal pasteurization technology:

1) Thermal pasteurization processes destroy some of the natural ingredients of the drink sometimes requiring the drink to be reformulated post disinfection to provide an acceptable tasting drink for the public. Often this requires chemical additives.

2) The taste of the drink is generally degraded from its original flavour.

3) A substantial amount of energy is required to thermally pasteurize a liquid.

4) The thermal energy required to pasteurize the drink is often removed by refrigeration before the bottling operation: this is a very energy inefficient and costly process.

5) Thermal pasteurizers require regular cleaning because some constituents of the drink bake onto the inside of the heat exchanger in the thermal pasteurizer and must be removed.

6) Drinks manufacturers often develop drinks which have market potential only to find that the drink is destroyed in the thermal pasteurization process.

7) The thermal pasteurization process does not kill all of the micro organisms encountered in the drink products e.g. the spores of alicyclobacillus, a spoilage organism effecting apple and orange juice, are unaffected by the thermal pasteurization process and can result in danger to public health and major product recalls for the drinks manufacturers.

It is well known that UV wavelengths in the range 220 nm-280 nm (germicidal wavelengths) kill all micro organisms. Such wavelengths will only disinfect if sufficient radiation penetrates the liquid. The liquids in the drinks industry are generally high absorbers of UV germicidal radiation (220 nm to 280 nm) and therefore UV light penetration into these liquids at such wavelengths is poor. For example the penetration of 254 nm though milk is very poor, with 90% of the incident radiation being absorbed in the first 0.01 mm penetration.

WO2006106363 and EP2055317 disclose apparatus which attempt to solve this problem by creating a thin film of the liquid to be treated and exposing the film to UV light in the germicidal wavelength. When semi opaque liquids are formed into thin films the UV light penetration at the germicidal wavelengths increases, this is a partial solution but dense liquids such as milk or sauces cannot be disinfected by this UV light, thin film irradiation technique alone. For high absorbing liquids the thin film must be thoroughly mixed as it is being disinfected, this diminishes the importance of UV light penetration and converts the process into substantially a UV surface disinfection technique.

Apparatus of the kind disclosed in WO2006106363 and EP2055317 have poor reliability due to complex mechanisms and many of moving parts. Furthermore the apparatus could not withstand the high pressures (up to 10 bar) used in the industry standard cleaning-in-place CIP process.

Patent no. US 2009081340, discloses an apparatus which comprises a stainless steel rotating inner cylinder and a stationary transparent outer cylinder. The liquid is introduced into the gap between the two cylinders and is irradiated by UV lamps through the stationary transparent outside cylinder. The intention of the rotating inner cylinder is to impart mixing to the liquid. The system is finely balanced with the throughput flow and the speed of rotation of the cylinder dictating the volume of liquid that can be disinfected, which for adequate mixing results in small volume throughput and hence is not commercial.

The rotating element requires that the thickness of the liquid film must be kept to a practical size for mechanical reliability requirements which conflicts with the principle of good disinfection of high absorber liquids i.e. thin liquid films for best light penetration, this system cannot be cleaned in place (CIP) as it cannot survive the high pressures (up to 10 bar) used in the industry standard CIP process.

The foregoing are problems which are common to previous attempts to solve the UV disinfection of semi opaque and opaque liquids.

The object of the present invention is to provide a low temperature disinfection system, with no moving parts and which can withstand the industry cleaning pressures. The present invention must be able to produce a consistent thin film of liquid which is continually and thoroughly mixed as the liquid flows through the system in high volumes.

I have now devised a disinfection apparatus for high UV absorber fluids which does not rely on thermal pasteurization and meets the aforementioned criteria.

In accordance with the invention there is provided a fluid treatment apparatus, comprising an elongate tubular duct having a fluid inlet and outlet at opposite ends thereof an elongate source of UV radiation extending longitudinally of said elongate tubular duct, and a mixing device disposed between adjacent longitudinal portions of the duct for diverting all of the fluid flowing along a first said portion of the duct through fluid mixing means in the device and for returning the mixed fluid to a second said portion of the duct.

The mixing of all the fluid ensures that all parts of the fluid come within sufficient proximity of the UV source.

Preferably said mixing means defines a tortuous flow path through which the fluid flows, the flow along the passage serving to provide a high degree of mixing.

Preferably the flow path comprises one or more turns of 90° and preferably the flow passage turns the fluid though at least 180° between adjacent longitudinal portions of the duct. Good mixing of a liquid can be achieved by continually changing its direction through 90° bends or preferably through 180° bends. The continual sudden velocity changes imparted to the liquid by this technique ensures all constituents of the liquid are mixed.

Preferably at least a portion of the flow path is arranged to be irradiated by UV radiation emitted by said source.

Preferably the duct defines a flow passage for the fluid in which all of the fluid is no more than 10 mm and preferably no more than 5 mm away from the surface of the UV source, the source forming at least a portion of the longitudinal wall of the flow passage. In this way the fluid flows as a thin film over the UV source. The surface constituents of the thin film are continually being changed due to the mixing effect.

Preferably the UV source extends along the central axis of the duct and is surrounded by the flow passage.

Preferably the UV source comprises an elongate lamp disposed inside a tube which is preferably formed of quartz or another material which is a good transmitter of UV radiation.

Preferably the tube is coated or covered with a material arranged to maintain the integrity of the tube should it break, thereby preventing contamination of the fluid with potential harmful pieces of the tube material. Preferably the coating or covering material comprises fluorinated ethylene propylene.

Preferably a plurality of said devices are provided along the length of the duct so that the fluid is mixed more than once.

Preferably the inlet and outlet communicate with respective manifolds at opposite ends of the duct.

Preferably the UV source extends into one or both manifolds.

Also, in accordance with the invention, there is provided a fluid disinfection system comprising a plurality of the above-mentioned apparatus connected in series to increase the disinfection effect or in parallel to increase the flow rate of the disinfected fluid or both.

A summarisation of the invention and the benefits thereof is as follows:

Disinfection system with no moving parts—all parts are stationary therefore the reliability of the system is high.

Room temperature (change to cold) disinfection system—the process is substantially a cold process.

Can withstand the industry cleaning pressures—all parts are able to withstand pressures of 10 bar and beyond.

Produces a consistent thin film of liquid—the gap between the quartz tube and the inner surface of the duct provides a consistent liquid film thickness.

Continually and thoroughly mixes the fluid—The mixing devices are placed at intervals along the length of the apparatus forcing the fluid to change direction and hence the fluid velocity ensuring constant and thorough mixing of the fluid as it flows through the system.

Embodiments of this invention will now be described by way of examples only and with reference to the accompanying drawings, in which.

Figure 1:
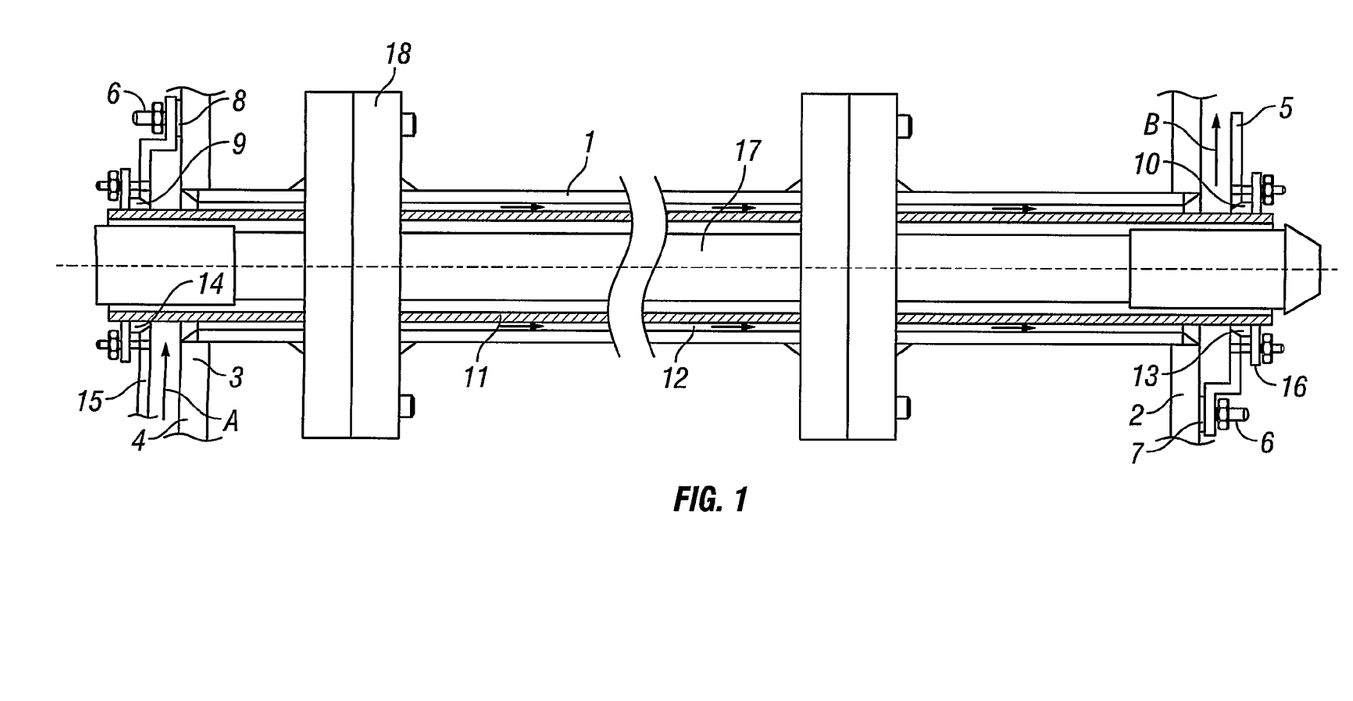
FIG. 1 shows a plan view with part section of a first embodiment of fluid disinfection apparatus in accordance with the invention.

Referring to FIG. 1 of the drawings in the first embodiment of the fluid disinfection apparatus a reaction chamber 1 is connected between end plates 2 & 3. Preferably the reaction chamber is welded to the end plates such that the welds are polished to provide a hygienic food grade seal.

Positioned adjacent to the reaction chamber is an inlet manifold 4 and an outlet manifold 5 which are attached to the end plates 2 & 3 by fastenings 6. The inlet manifold 4 and outlet manifold 5 are made watertight by seals 7 & 8 which are clamped between the inlet and outlet manifolds 4 & 5 and the end plates 2 & 3.

A tubular sleeve 11 is positioned longitudinally centrally and concentrically inside the reaction chamber 1 such that it protrudes through the end plates 2 & 3 and through the holes 9 & 10 in the inlet and exit manifolds 4 & 5.

Preferably the tubular sleeve is a good transmitter of the germicidal wavelengths (220 nm-280 nm).

Preferably the tubular sleeve is made of quartz.

Preferably the quartz sleeve is coated with a material which substantially transmits the germicidal wavelengths.

Preferably the coating material is substantially resilient in nature and is able to contain all quartz debris in the event of the quartz tube rupturing.

Preferably the material is Teflon FEP.

Means are provided to form a small concentric gap 12 between the tubular sleeve 11 and the inside wall of the reaction chamber 1. By selecting the dimensions of the outer diameter of the tubular sleeve 11 to be slightly smaller than the inner diameter of the reaction chamber 1, the gap 12 produced is the dimensional difference between the two.

Means are provided to make a water tight seal between the tubular sleeve 11 and the inlet and outlet manifolds 4 & 5 in the form of a seal 13 & 14 positioned on the circumference at each end of the tubular sleeve 11 adjacent to the holes 9 & 10 in the inlet and outlet manifolds 4 & 5. The seal is compressed by clamping plates 15 & 16 forming a watertight seal between the inlet and outlet manifolds 4 & 5 and the tubular sleeve 11.

The reaction chamber 1, tubular sleeve 11 and the inlet and outlet manifolds 4 & 5 form a watertight assembly such that liquid can flow in through the inlet manifold 4, through the gap 12 and out through the outlet manifold 5.

Preferably the seals 13 & 14 are made of UV resistant material.

Preferably the material is silicone rubber, Viton, PTFE or Teflon FEP.

Preferably the seals 13 & 14 are designed to be flexible such that any differential expansion between the body of the reaction chamber 1 and the tubular sleeve 11 is accommodated whilst the seals 13 & 14 still remain sealed.

Means are provided to radiate UV germicidal wavelengths (220 nm-280 nm) into the gap 12 in the form of a UV lamp 17 positioned inside the tubular sleeve 11 which when energised radiate germicidal wavelengths into the gap through the wall of the tubular sleeve 11.

Preferably the lamp 17 is positioned longitudinally centrally and concentrically inside the tubular sleeve 11 to provide consistent and even radiation into the gap 12.

Means are provided to mix the liquid as it passes through the disinfector in the form of mixing devices 18 positioned along the body of the reaction chamber 1 whereby the flow in the gap 12 is diverted into and through the mixing device 18. The mixing device 18 forces the liquid to traverse a flow path which causes it to change direction and hence velocity to create a thorough mixing of the fluid as it passes through the device.

Preferably the mixing device 18 has no moving parts.

Preferably the mixing device 18 forces the liquid into at least one 180° bend

Preferably the mixing device 18 is made of material which is substantially resistant to germicidal radiation.

Preferably the outside body of the mixing device 18 is made of a food grade standard material.

Preferably the outside body of the mixing device 18 is made of 316 grade stainless steel.

Preferably the internal materials of the mixing device 18 are made of PTFE or Teflon FEP or another suitable material.

The general fluid flow is shown by the arrows A & B and the intervening arrows.

Figure 5:
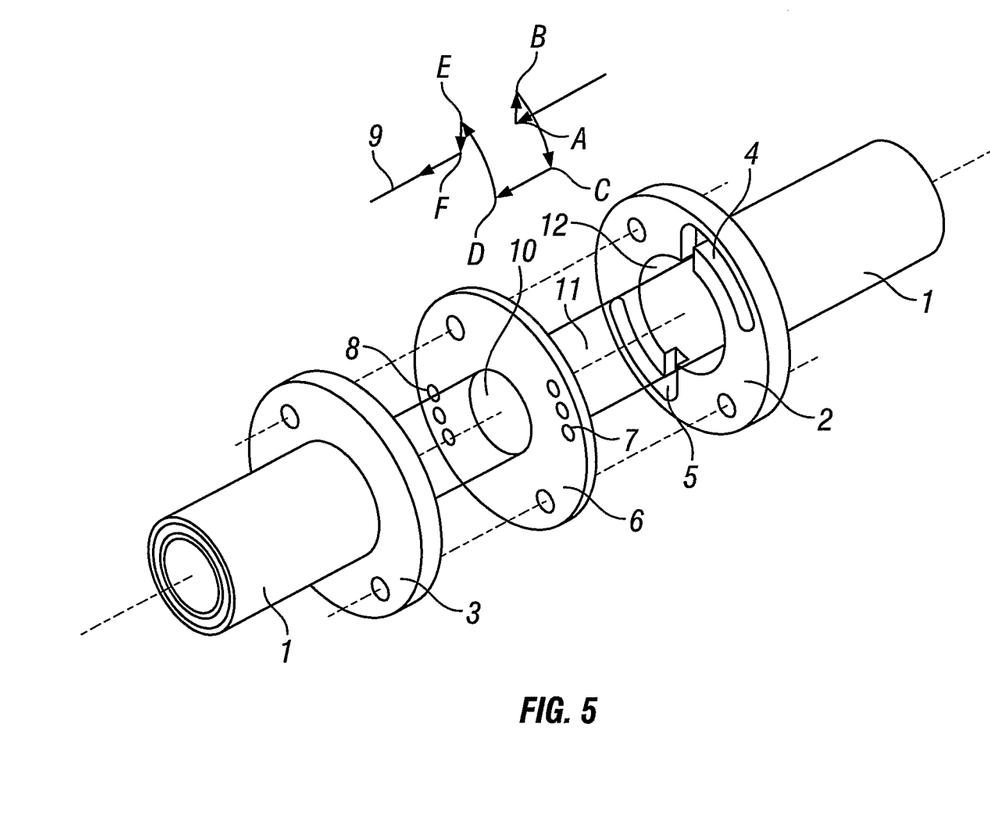
FIG. 5 shows an exploded view of another kind of mixing device for a fluid disinfection apparatus in accordance with the invention.

Referring to FIG. 5 of the drawings shows a mixing device for the apparatus comprising circular flanges 2 & 3 attached to the body of the reaction chamber 1.

Flange 2 has shallow grooves cut into its face which act as channels for the liquid. The top groove 4 rises vertically from the centre of the flange 2 then moves in an arc in a clockwise direction for a distance around the top face of the flange 2. The bottom groove 5 falls vertically from the centre of the flange 2 then moves in an arc in a clockwise direction for a distance around the bottom face of the flange 2.

Flange 3 has a mirror pattern of grooves (not shown) cut into its face such that the grooves match each other when the flanges are fastened together.

Positioned through the centre of the reaction chamber 1 is the tubular sleeve 11 as described previously, which with the reaction chamber 1 provides the gap 12.

Interposed between the two flanges is a disc 6 which has a series of holes 7 & 8 positioned so that they line up with the ends of the clockwise arcs in the two flanges 2 & 3 when the mixing device is assembled. The centre hole 10 in the disc 6 is a tight fit on the tubular sleeve 11. When the mixing device is assembled the disc 6 substantially acts as a deflector for the liquid in the gap 12 diverting it out of the gap 12 and into the grooves 4 & 5 and holes 7 & 8.

Assuming that the liquid is moving from right to left in gap 12 of the reaction chamber 1, the disc will force the liquid into the grooves 4, in flange 2, through the holes 7 & 8 in the disc 6 and back along the mirrored grooves in flange 3 and into the gap 12 in the reaction chamber 1.

A flow schematic sketch 9 shows the fluid path through the device

The liquid will have had three complete reversals of flow through the mixing device. A—90° change in direction from the gap 12 to the vertical groove on flange 2, B—90° change in direction from vertical groove on flange 2 to the clockwise arc on flange 2, C—90° change in direction from the clockwise arc on flange 2 to the holes 7 in the disc 6, D—90° change in direction from the holes 7 in the disc 6 into the mirrored arc in flange 3, E—90° change in direction from the mirrored arc in flange 3 to the mirrored vertical groove in flange 3, F—90° change in direction from the mirrored vertical groove in flange 3 to the gap 12.

Preferably the disc is made of a UV resistant material.
Preferably the disc is made from PTFE or Teflon FEP The mixing device has an additional feature in that after CIP (clean in place—the drinks industry standard cleaning process) the unit self sterilizes if at the end of the cleaning cycle it is filled with water and the lamp is switched on for a period of time, there is enough radiation to reflect through the mixing device to disinfect it.

FIG. 5 only shows one disc 6 but a plurality of discs can be positioned in series to increase the level of mixing of the fluid.

Those skilled in the art will appreciate that the mixing effect can be accomplished with many different labyrinths like patterns in the mixing device of which the general theory of the invention covers.

Figure 2:
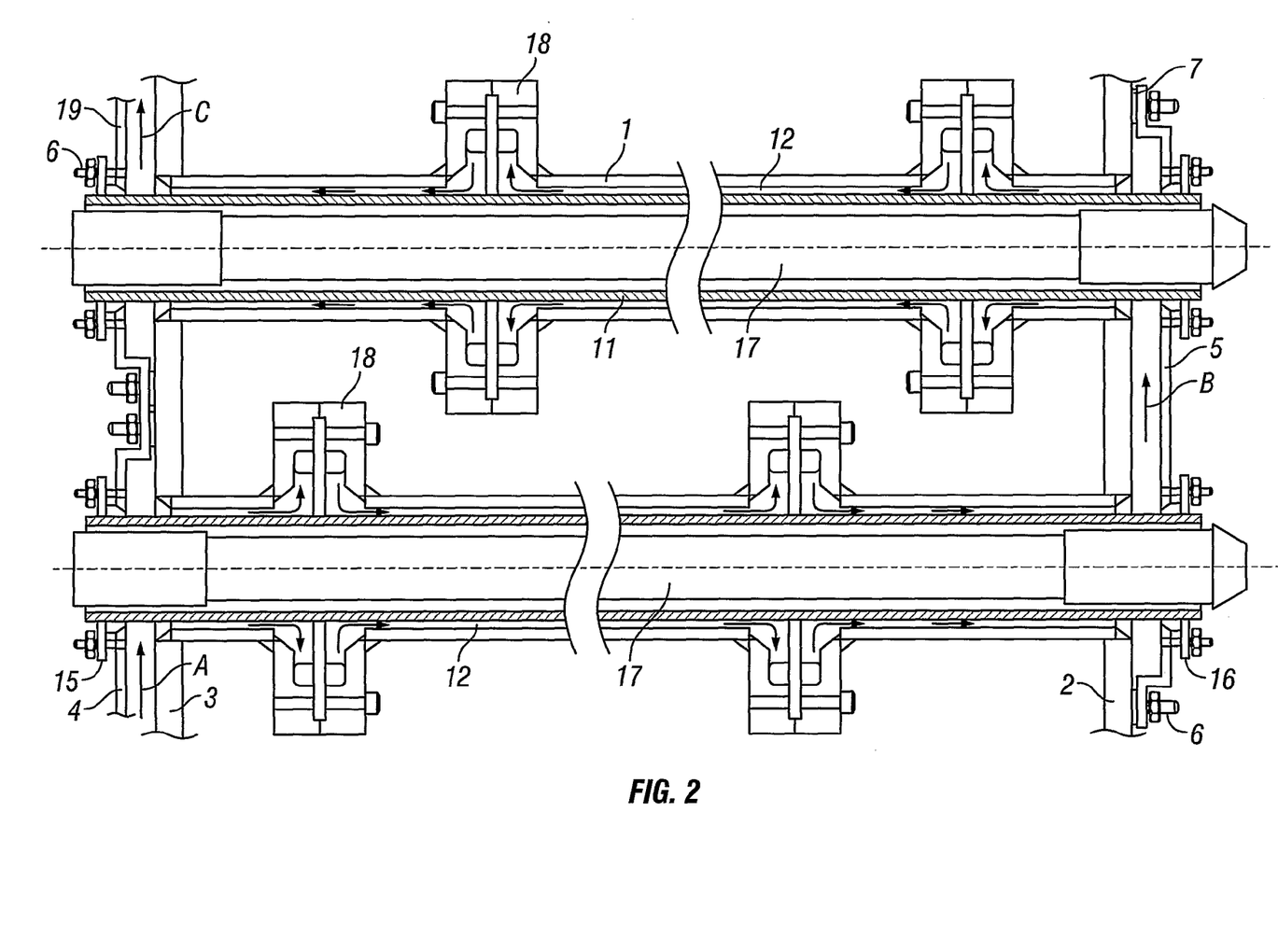
FIG. 2 shows a plan view with part section of a second embodiment of fluid disinfection apparatus in accordance with the invention.

Referring to FIG. 2 of the drawings there is shown a second embodiment of a mixing device apparatus comprising a plurality of fluid disinfection apparatuses as described previously but whose inlet and outlet manifolds 5 & 6 act as conduits to allow the fluid disinfection apparatus to be connected in series.

Fluid flows from A into the gap 12 and then into the first mixing device 18 in the first fluid disinfection apparatus and continues along the gap 12 and through each mixing device 18 in turn until it flows into the exit manifold 5. The fluid then flows through the exit manifold 5 and into the gap 12 of the second fluid disinfection apparatus and the then flows in turn through each mixing device 18 in the second fluid disinfection apparatus until it reaches the second fluid disinfection apparatus's exit manifold 19.

The process repeats for as many fluid disinfection apparatuses are connected together.

As the fluid passes through the gap 12 it is irradiated by the germicidal wavelengths radiating from the UV lamp 17 and through the wall of the tubular sleeve 11 to provide a very effective disinfection of the fluid film.

Several of these fluid disinfection apparatus arrays can be connected together in parallel to increase the flow handling capability of the system.

Figure 3:
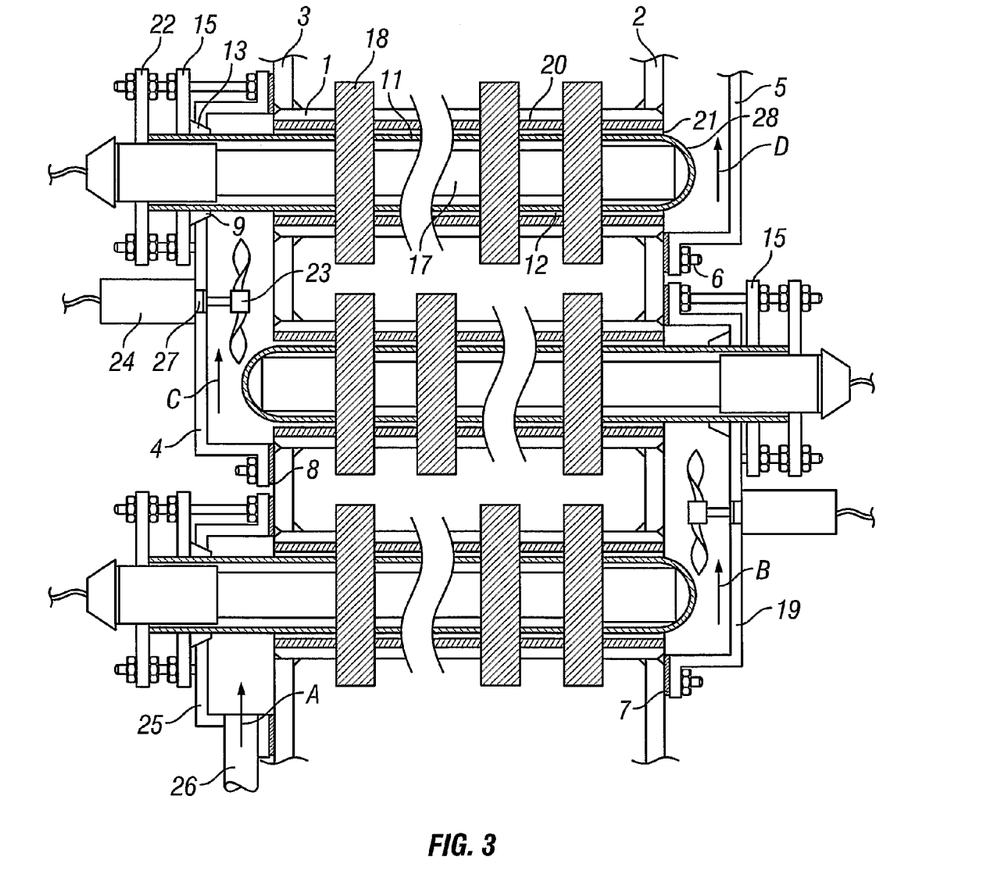
FIG. 3 shows a plan view with part section of a third embodiment of fluid disinfection apparatus in accordance with the invention.

Referring to FIG. 3 of the drawings showing the third embodiment of the fluid disinfection apparatus, a plurality of fluid disinfection apparatuses are constructed such that the fluid disinfection apparatuses are connected in series. Each fluid disinfection apparatus feeds it flow into another fluid disinfection apparatus.

Each fluid disinfection apparatus consists of a reaction chamber 1 rigidly connected between end plates 2 & 3.

Preferably the reaction chamber is welded to the end plates such that the welds are polished to provide a hygienic food grade seal.

Positioned adjacent to the reaction chamber is an inlet manifold 4 and an outlet manifold 5 which are attached to the end plates by fastenings 6. The inlet manifold 4 and outlet manifold 5 are made watertight by seals 7 & 8 which are clamped between the inlet and outlet manifolds 4 & 5 and the end plates 2 & 3.

A tubular sleeve 11 is positioned longitudinally centrally and concentrically inside the reaction chamber such that it protrudes through the end plates 2 & 3 and through a hole 9 in the inlet manifold 4.

Preferably the tubular sleeve is a good transmitter of the germicidal wavelengths (220 nm-280 nm).

Preferably the tubular sleeve is made of quartz.

Preferably the tubular sleeve is closed at one end 28.

Preferably the quartz sleeve is coated with a material which substantially transmits the germicidal wavelengths (220 nm-280 nm).

Preferably the coating material is substantially resilient in nature and is able to contain all quartz debris in the event of the quartz tube rupturing.

Preferably the material is Teflon FEP.

Means are provided to form a small concentric gap 12 between the tubular sleeve 11 and the inside wall of the mixing sleeve 20. By selecting the dimensions of the outer diameter of the tubular sleeve 11 to be slightly smaller than the inner diameter of the mixing sleeve 20, the gap 12 produced is the dimensional difference between the two.

Means are provided to make a water tight seal between the tubular sleeve 11 and the inlet manifold 4 in the form of a seal 13 positioned on the circumference of the open end of the tubular sleeve 11 adjacent to a hole 9 in the inlet manifold. The closed end of the tubular sleeve 11 is supported by collar 21 and it is free to move inside the collar.

Any differential expansion between the reaction chamber 1 and the tubular sleeve 11 is automatically accommodated by this arrangement.

Under fluid pressure the tubular sleeve 11 with one end closed experiences a net force which acts such as to move the tubular sleeve 11 in the direction of the open end of the tube. To prevent tubular sleeve 11 movement under pressure the retaining plate 22 holds the tubular sleeve 11 in position preventing any movement.

The seal 13 is compressed by a clamping plate 15 forming a watertight seal between the inlet manifold 4 and the tubular sleeve 11. The reaction chamber 1, tubular sleeve 11 and the inlet and outlet manifolds 4 & 5 form a watertight assembly such that fluid can flow in through the inlet manifold 4, through the gap 12 and out through the outlet manifold 5.

Preferably the seal 13 is made of UV resistant material.

Preferably the material is silicone rubber, PTFE or FEP or another UV resistant material.

Means are provided to radiate UV germicidal wavelengths (220 nm-280 nm) into the gap 12 in the form of a lamp 17 positioned inside the tubular sleeve which when energised radiate germicidal wavelengths into the gap through the wall of the tubular sleeve.

Means are provided for mixing the liquid in the gap 12 in the form of a mixing sleeve 20 which is rigidly fixed in a watertight manner into the reaction chamber 1.

Preferably the mixing sleeve is pressed or glued onto the reaction chamber 1 forming a water tight seal.

Preferably in order to provide an additional mixing function to the fluid film, the inside surface of the mixing sleeve 20 adjacent to the tubular sleeve 11 is formed into a pattern which when the liquid flows through the gap 12 creates turbulence and hence mixing in the fluid film.

Preferably the lamp is positioned longitudinally centrally and concentrically inside the tubular sleeve to provide consistent and even radiation into the gap.

Means are provided to mix the fluid as it passes through the disinfector in the form of mixing devices 18 positioned along the body of the reaction chamber whereby the flow in the gap 12 is diverted into and through the mixing device. The mixing device 18 forces the fluid flow to traverse a path which causes the fluid to change direction and hence velocity to create a thorough mixing of the fluid as it passes through the device.

Preferably the mixing device 18 has no moving parts.

Preferably the mixing device 18 is made of material which is substantially resistant to germicidal radiation.

Preferably the mixing device 18 is made of a food grade standard material.

Preferably the body of the mixing device 18 is made of 316 standard stainless steel.

Preferably the internal parts of the mixing device 18 are made of PTFE, Teflon FEP or another suitable material.

Means are provided to add additional mixing in the form of a propeller 23 positioned through the wall of each of the inlet and outlet manifolds. The motor and gearbox 24 is fixed to the wall of each of the inlet and outlet manifolds and is supported by a bearing and seal 27. When actuated by the motor and gearbox 24 the propeller 23 rotates in the fluid flow and creates a high level of mixing.

The fluid to be disinfected enters into the apparatus via the inlet pipe 26 through the wall of the feed manifold 25

The general fluid flow is shown by the arrows A, B, C & D.

Figure 4:
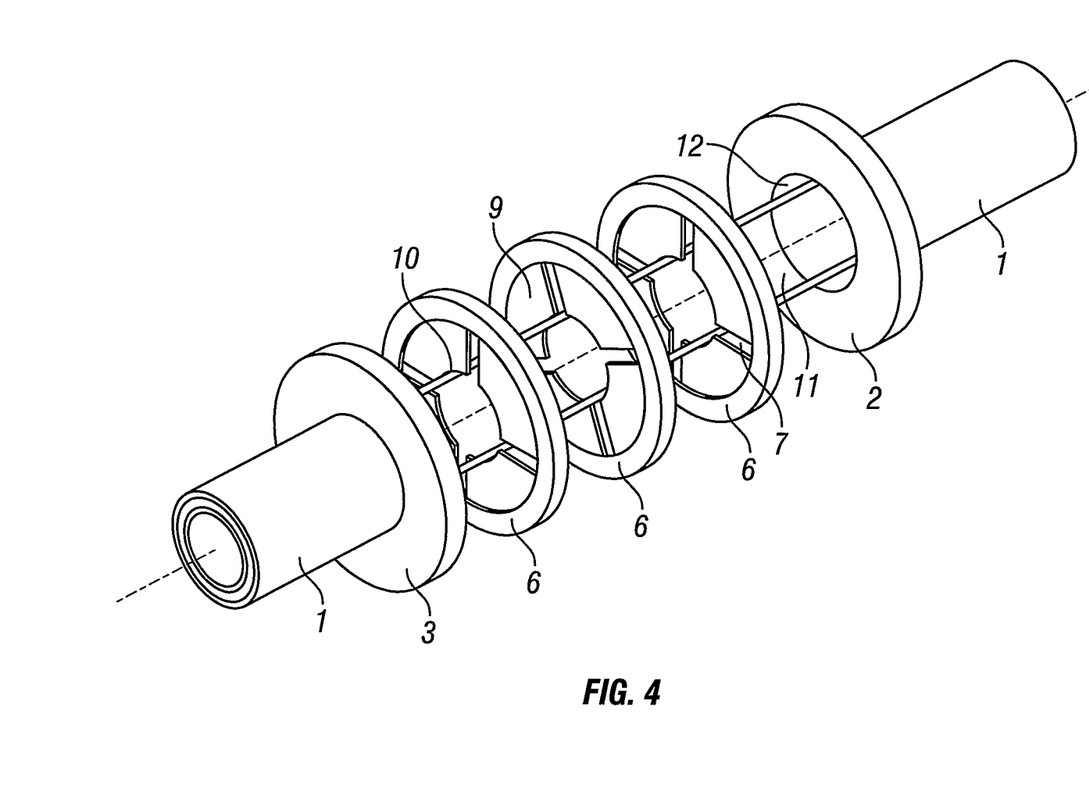
FIG. 4 shows an exploded view of one kind of mixing device for a fluid disinfection apparatus in accordance with the invention.

Referring to FIG. 4 of the drawings shows a mixing device for the apparatus comprises circular flanges 2 & 3 attached to the body of the reaction chamber 1. Both flange 2 and flange 3 have smooth faces Positioned through the centre of the reaction chamber 1 is the tubular sleeve 11 as described previously, which with the reaction chamber 1 provides the gap 12.

Interposed between the two flanges is a plurality of discs 6 each disc has a series of slots 7 cut into the disc 6 radially from the centre outwards and positioned equi-distance around the circumference of the disc 6. Each disc 6 is positioned so that the slots in alternative discs are equi-spaced between the slots in the proceeding disc 6 such when the discs 6 are assembled together they form a labyrinth i.e. there is no straight fluid path through the assembled discs. Preferably the disc patterns are made and assembled such that the resulting labyrinth causes a fluid flowing through it to be forced to perform 180° bends. The centre hole 10 in the disc 6 is a tight fit on the tubular sleeve 11 which when the mixing device is assembled the walls 9 of the disc 6 substantially acts as a deflector for the fluid diverting it out of the gap 12 and forcing it through the slots 7 and through the labyrinth.

Preferably the fluid will have had many complete reversals of flow through the mixing device creating a thorough mixing of the fluid.

Preferably the discs 6 are made of a UV resistant material.

Preferably the disc is made from PTFE or Teflon FEP

The mixing device has an additional feature in that after CIP (clean in place—the drinks industry standard cleaning process) the unit self sterilizes if at the end of the cleaning cycle if it is filled with water and the lamp is switched on for a period of time, there is enough radiation to reflect through the mixing device to disinfect it.

FIG. 4 only shows three discs 6 but a plurality of discs can be positioned in series to increase the level of mixing of the fluid.

Those skilled in the art will appreciate that the mixing effect can be accomplished with many different labyrinth-like patterns in the mixing device of which the general theory of the invention covers.

It should be noted that known static mixers do not create flow reversal i.e. 180° bend: they blend a liquid by manipulating it always in a forward direction and hence need a sizable longitudinal component to effect the mixing. The mixing devices in this invention effect the mixing over a short distance by flow reversal and hence a plurality of mixing devices can be employed over a short distance.

Figure 6:
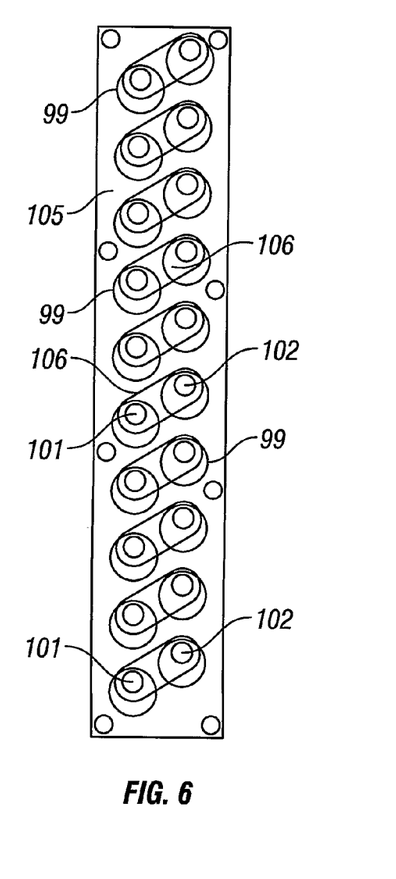
FIG. 6 shows a sectional view of a fourth embodiment of fluid disinfection apparatus in accordance with the invention.

Referring to FIGS. 6 an 7 of the drawings, a fluid treatment system comprises twenty plurality of fluid treatment apparatus 99 of the kind disclosed in FIG. 1 mounted side-by-side in a housing 105. Each apparatus 100 comprises an elongate tubular duct 100 having a fluid inlet and outlet 101,102 at opposite ends thereof an elongate source of UV radiation 104 extending longitudinally of the elongate tubular duct 100. A plurality of mixing devices 103 of the kind disclosed in FIG. 4 or 5 are disposed between adjacent longitudinal portions of each duct 100 for diverting all of the fluid flowing along the duct through fluid mixing formations in the device 103 and for returning the mixed fluid to the duct.

Figure 7:
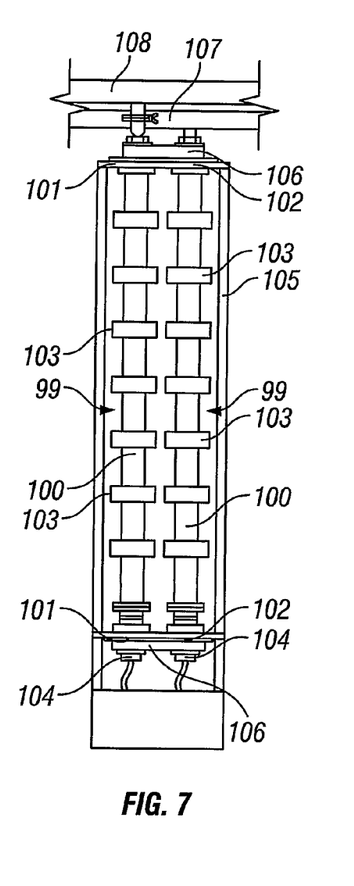
FIG. 7 shows a plan view of the apparatus of FIG. 6.

The outlet and inlets 101, 102 of adjacent apparatus 99 are connected to each other via respective manifolds 106. In use, fluid flows downwardly from an inlet duct 107 into the first apparatus 100 and then through a manifold 106 and upwardly through a second apparatus 100 and so on until the fluid flows out of the last apparatus 99 into an outlet duct 108.

Figure 8:
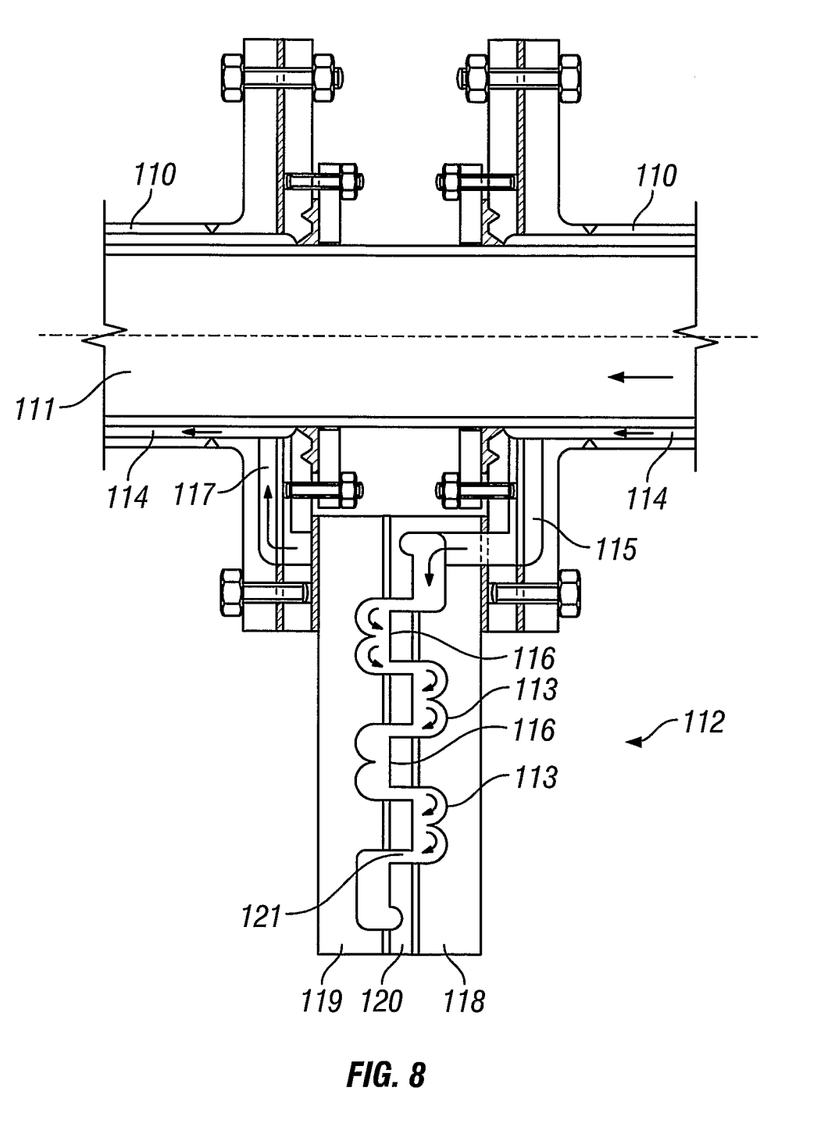
FIG. 8 shows an exploded view of a portion of fifth embodiment of fluid disinfection apparatus in accordance with the invention.

Referring to FIG. 8 of the drawings, a fluid treatment comprises an elongate tubular duct 110 having an elongate source of UV radiation 111 extending longitudinally of the elongate tubular duct 110. A plurality of mixing devices 112 are sealingly fitted between disposed between adjacent longitudinal portions the duct 110 for diverting all of the fluid flowing along the duct 110 through fluid mixing formations 113 in the device 112 and for returning the mixed fluid to the duct 110.

Each device 112 depends from the duct 110 and is mounted entirely below the level of the flow passage 114 therein to ensure that no high spots exist in which air may become trapped. The device 112 comprises a flow path having an inlet duct 115 which extends perpendicular to the longitudinal flow axis of the passage 114. The path then comprises a series of formations 113 which turn the fluid flow through 180° and direct it at a baffle wall where it is deflected into another formation 113 ensuring that the fluid is thoroughly mixed. Fluid then leaves the device 112 through a flow an outlet duct 117 which extends perpendicular to the longitudinal flow axis of the next section of the passage 114.

The formations 113 are formed in the opposing faces of plates 118,119 which are clamped together against a central plate 120 formed with apertures 121 that communicate between the formations 113. The plate 120 and or plates 119,120 may be formed of a material which transmits UV radiations so that the flow path is sterilised by the radiation from the UV source 111.

Figure 9:
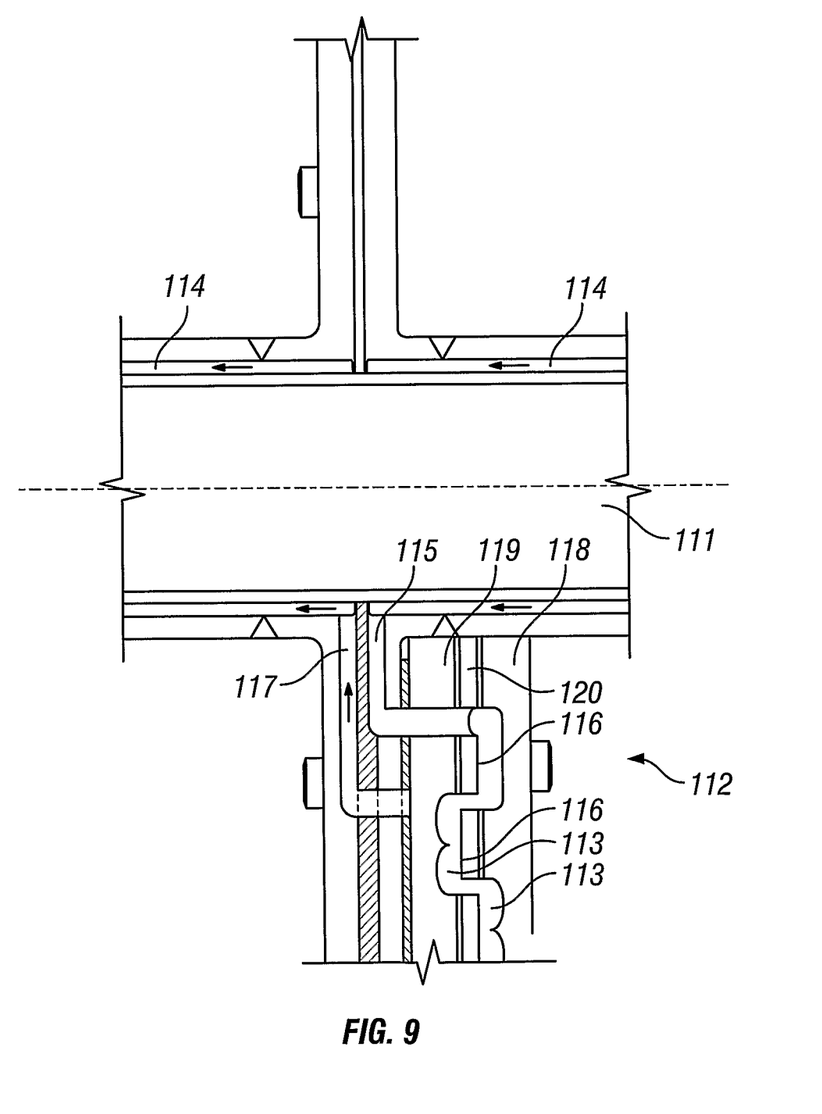
FIG. 9 shows an exploded view of a portion of sixth embodiment of fluid disinfection apparatus in accordance with the invention.

Referring to FIG. 9 of the drawings, there is shown an embodiment which is similar to the embodiment of FIG. 8 but which is simpler in construction.

The presention invention thus provides a fluid treatment apparatus particularly for sterilising drinks which comprises an elongate tubular duct and an elongate UV light source extending longitudinally of the duct. A mixing device disposed between adjacent longitudinal portions of the duct diverts all of the fluid flowing along a first portion of the duct through fluid mixing means in the device and returns the mixed fluid to a second portion of the duct. The fluid flows longitudinally of the duct in a thin annular low passage which extends around the UV light source. Micro-organisms in the resultant thin flow of fluid are killed as they come within close proximity of the light source. The mixing device causes all of the flow to be thoroughly mixed and returned to the flow passage. The preferred provision of a plurality of mixing devices along the length of the duct increases the likelihood that all microorganisms receive a sufficient lethal dose of UV radiation.

The invention claimed is:

1. A fluid treatment apparatus comprising an elongate tubular duct having a fluid inlet and a fluid outlet at opposite ends thereof an elongate source of UV radiation extending longitudinally of said elongate tubular duct, and a mixing device disposed between adjacent longitudinal portions of the duct diverting all of the fluid flowing along a first one of said portions of the duct through a fluid mixer in the mixing device and for returning the mixed fluid to a second one of said portions of the duct.

2. A fluid treatment apparatus as claimed in claim 1, in which said mixer comprises a tortuous flow path defined by the fluid mixer through which the fluid flows.

3. A fluid treatment apparatus as claimed in claim 2 in which the flow path defined by the fluid mixer comprises one or more baffles against which the flow is directed.

4. A fluid treatment apparatus as claimed in claim 2 in which the flow path is arranged to be irradiated by UV radiation emitted by said source.

5. A fluid treatment apparatus as claimed in claim 1, in which the flow path defined by the fluid mixer comprises one of more turns of at least 90°.

6. A fluid treatment apparatus as claimed in claim 5, in which the flow path defined by the fluid mixer turns the fluid through 180° between adjacent longitudinal portions of the duct.

7. A fluid treatment apparatus as claimed in claim 6, in which the flow path defined by the fluid mixer successively turns the fluid through 180° between adjacent longitudinal portions of the duct.

8. A fluid treatment apparatus as claimed in claim 1, in which the duct defines a flow passage for the fluid which is arranged to contain all of the fluid at no more than 10 mm away from the surface of the UV source.

9. A fluid treatment apparatus as claimed in claim 8, in which the duct defines a flow passage for the fluid which is arranged to contain all of the fluid at no more than 5 mm away from the surface of the UV source.

10. A fluid treatment apparatus as claimed in claim 8, in which the UV source extends along the central axis of the duct and is surrounded by the flow passage.

11. A fluid treatment apparatus as claimed in claim 1, in which the UV source comprises an elongate lamp disposed inside a tube.

12. A fluid treatment apparatus as claimed in claim 11, in which the tube is coated or covered with a material arranged to maintain the integrity of the tube should it break.

13. A fluid treatment apparatus as claimed in claim 1, in which a plurality of said mixing devices are provided along the length of the duct.

14. A fluid treatment apparatus as claimed in claim 1, in which the inlet and the outlet communicate with respective manifolds at opposite ends of the duct.

15. A fluid treatment apparatus as claimed in claim 14, in which the UV source extends into one or both manifolds.

16. A fluid treatment apparatus as claimed in claim 15, in which at least one of the manifolds comprises means for further mixing the fluid.

17. A fluid disinfection system comprising a plurality of fluid treatment apparatuses as claimed in claim 1, connected in series.

18. A fluid disinfection system as claimed in claim 17 comprising a plurality of fluid treatment apparatuses as claimed in claim 1 connected in parallel.

19. A fluid treatment apparatus as claimed in claim 1, in which said mixer comprises a tortuous flow path defined by the fluid mixer through which the fluid flows, the tortuous flow path forming a labyrinth-like pattern.

20. A fluid treatment apparatus comprising:
a fluid transport means for transporting a fluid flow;
a UV irradiation means for irradiating fluid flowing in said fluid transport means; and
a mixing means for mixing fluid flowing in said fluid transport means and diverting all of the fluid flowing along a first portion of a duct to a second portion of the duct.

21. A fluid treatment apparatus according to claim 20 in which said mixing means comprises a tortuous flow path through which the fluid flows.

* * * * *

UNITED STATES PATENT AND TRADEMARK OFFICE
CERTIFICATE OF CORRECTION

PATENT NO. : 8,742,366 B2  Page 1 of 1
APPLICATION NO. : 13/266444
DATED : June 3, 2014
INVENTOR(S) : Malcolm Robert Snowball It is certified that error appears in the above-identified patent and that said Letters Patent is hereby corrected as shown below:

On the title page, item (56) OTHER PUBLICATIONS: delete "Corrperation" and insert --Corporation--

Signed and Sealed this
Second Day of September, 2014

Michelle K. Lee
*Deputy Director of the United States Patent and Trademark Office*